(12) United States Patent
Baumgarten et al.

(10) Patent No.: US 9,353,040 B2
(45) Date of Patent: May 31, 2016

(54) METHOD AND DEVICE FOR THE HYDROFORMYLATION OF ISOBUTENE AND FOR THE SEPARATION OF THE PRODUCT MIXTURE

(71) Applicants: Goetz Baumgarten, Haltern am See (DE); Michael Graß, Haltern am See (DE); Alfred Kaizik, Marl (DE); Markus Winterberg, Datteln (DE); Hans-Gerd Lueken, Marl (DE); Bart Hamers, Horst (NL); Markus Priske, Mobile, AL (US); Dirk Fridag, Haltern am See (DE); Robert Franke, Marl (DE); Dieter Hess, Marl (DE)

(72) Inventors: Goetz Baumgarten, Haltern am See (DE); Michael Graß, Haltern am See (DE); Alfred Kaizik, Marl (DE); Markus Winterberg, Datteln (DE); Hans-Gerd Lueken, Marl (DE); Bart Hamers, Horst (NL); Markus Priske, Mobile, AL (US); Dirk Fridag, Haltern am See (DE); Robert Franke, Marl (DE); Dieter Hess, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/380,647

(22) PCT Filed: Feb. 11, 2013

(86) PCT No.: PCT/EP2013/052633
§ 371 (c)(1),
(2) Date: Aug. 22, 2014

(87) PCT Pub. No.: WO2013/124176
PCT Pub. Date: Aug. 29, 2013

(65) Prior Publication Data
US 2015/0018576 A1     Jan. 15, 2015

(30) Foreign Application Priority Data
Feb. 23, 2012  (DE) .......................... 10 2012 202 779

(51) Int. Cl.
| | |
|---|---|
| C07C 51/43 | (2006.01) |
| C07C 45/78 | (2006.01) |
| C07C 45/50 | (2006.01) |
| C07C 51/235 | (2006.01) |
| B01D 61/02 | (2006.01) |
| C07C 45/82 | (2006.01) |

(52) U.S. Cl.
CPC .............. *C07C 51/43* (2013.01); *B01D 61/027* (2013.01); *C07C 45/50* (2013.01); *C07C 45/505* (2013.01); *C07C 45/786* (2013.01); *C07C 45/82* (2013.01); *C07C 51/235* (2013.01)

(58) Field of Classification Search
CPC ...... C07C 51/43; C07C 51/235; C07C 45/82; C07C 45/50; C07C 45/786; C07C 45/505
See application file for complete search history.

(56) References Cited

U.S. PATENT DOCUMENTS

| | | | |
|---|---|---|---|
| 6,482,992 B2 | 11/2002 | Scholz et al. |
| 6,500,991 B2 | 12/2002 | Wiese et al. |
| 6,960,699 B2 | 11/2005 | Tötsch et al. |
| 7,138,552 B2 | 11/2006 | Kaizik et al. |
| 7,154,012 B2 | 12/2006 | Lueken et al. |
| 7,179,947 B2 | 2/2007 | Lueken et al. |
| 7,193,116 B2 | 3/2007 | Moeller et al. |
| 7,232,931 B2 | 6/2007 | Toetsch et al. |
| 7,317,130 B2 | 1/2008 | Möller et al. |
| 8,129,571 B2 | 3/2012 | Lueken et al. |
| 8,138,379 B2 | 3/2012 | Lueken et al. |
| 8,226,829 B2 | 7/2012 | Wiese et al. |
| 8,389,774 B2 | 3/2013 | Becker et al. |
| 8,404,902 B2 | 3/2013 | Kreidler et al. |
| 8,415,520 B2 | 4/2013 | Winterberg et al. |
| 8,461,394 B2 | 6/2013 | Lueken et al. |
| 8,748,643 B2 | 6/2014 | Priske et al. |
| 8,884,070 B2 | 11/2014 | Franke et al. |
| 8,999,038 B2 | 4/2015 | Ungerank et al. |
| 9,149,780 B2 | 10/2015 | Hamers et al. |
| 2007/0135665 A1 | 6/2007 | Wiese et al. |
| 2008/0251456 A1 | 10/2008 | Wiese et al. |
| 2009/0032465 A1 | 2/2009 | Baumgarten et al. |
| 2009/0163687 A1 | 6/2009 | Kaizik et al. |
| 2010/0048959 A1 | 2/2010 | Sigl et al. |
| 2012/0035382 A1 | 2/2012 | Priske et al. |
| 2012/0046503 A1 | 2/2012 | Priske et al. |

(Continued)

FOREIGN PATENT DOCUMENTS

| | | | |
|---|---|---|---|
| DE | 10 2005 046 250 A1 | 3/2007 |
| EP | 1 103 303 | * | 5/2001 |

(Continued)

OTHER PUBLICATIONS

U.S. Appl. No. 10/588,762, filed Jan. 10, 2007, Wiese, et al.

(Continued)

*Primary Examiner* — Shailendra Kumar
(74) *Attorney, Agent, or Firm* — Oblon, McClelland, Maier & Neustadt, L.L.P.

(57) ABSTRACT

The invention relates to a method for producing a product mixture (2) by means of the technical hydroformylation of a hydrocarbon stream (1) that contains isobutene, and for separating the product mixture (2) that is obtained, as well as to a device for the claimed method and to the use of a claimed device. The problem addressed thereby is that of providing a method and an associated device that allow the amount of high-boiling substances in the product mixture (2) to be kept as low as possible and thus the yield of the reaction to be increased. The problem is solved by the use of a nano-filtration device (M) for separating the catalyst from the product mixture (2), said device having especially high permeability to 3-methylbutanoic acid.

20 Claims, 3 Drawing Sheets

(56) References Cited

U.S. PATENT DOCUMENTS

2012/0123079 A1    5/2012    Ungerank et al.
2012/0279922 A1    11/2012    Haensel et al.

FOREIGN PATENT DOCUMENTS

| | | |
|---|---|---|
| WO | WO 2008/006633 A1 | 1/2008 |
| WO | WO 2014/056732 A1 | 4/2014 |
| WO | WO 2014/095452 A1 | 6/2014 |

OTHER PUBLICATIONS

U.S. Appl. No. 12/159,957, filed Jul. 2, 2008, Baumgarten, et al.
U.S. Appl. No. 13/203,639, filed Oct. 4, 2011, Priske, et al.
U.S. Appl. No. 13/384,685, filed Jan. 18, 2012, Ungerank, et al.
U.S. Appl. No. 13/513,225, filed Jul. 24, 2012, Haensel, et al.
English translation of the International Search Report issued May 24, 2013, in PCT/EP2013/052633.
U.S. Appl. No. 14/653,717, filed Jun. 18, 2015, Fridag, et al.
U.S. Appl. No. 14/435,052, filed Apr. 10, 2015, Fridag, et al.
U.S. Appl. No. 14/435,007, filed Apr. 10, 2015, Christiansen, et al.
U.S. Appl. No. 14/434,988, filed Apr. 10, 2015, Christiansen, et al.
U.S. Appl. No. 14/434,879, filed Apr. 10, 2015, Christiansen, et al.
U.S. Appl. No. 14/434,827, filed Apr. 10, 2015, Christiansen, et al.
Search Report issued Jun. 16, 2015 in Singaporean Application No. 11201404917W, filed Feb. 11, 2013.
Written Opinion issued Jun. 16, 2015 in Singaporean Application No. 11201404917W, filed Feb. 11, 2013.
U.S. Appl. No. 14/380,647, filed Aug. 22, 2014, Baumgarten, et al.
U.S. Appl. No. 14/890,821, filed Nov. 12, 2015, Priske, et al.
U.S. Appl. No. 14/770,525, filed Aug. 26, 2015, Lueken et al.

\* cited by examiner

Fig. 3 ical scale hydroformylation, organophosphorus metal complex catalysts based on cobalt or rhodium are nowadays used. The catalysts are dissolved homogeneously in the liquid hydroformylation mixture. In the course of separation of the target product (of the aldehydes) from the hydroformylation mixture, the homogeneous catalyst also has to be removed gently from the hydroformylation mixture, since the complex catalyst is comparatively sensitive to changes in state and could lose its activity. Traditionally, the catalyst is separated by distillation from the hydroformylation mixture. In order to lower the risk of deactivation and to lower the energy consumption of the process, there have recently been efforts to separate the homogeneously dissolved catalyst from the hydroformylation mixture with the aid of membrane technology (nanofiltration).

METHOD AND DEVICE FOR THE HYDROFORMYLATION OF ISOBUTENE AND FOR THE SEPARATION OF THE PRODUCT MIXTURE

CROSS REFERENCE TO RELATED APPLICATIONS

This application is a National Stage of PCT/EP2013/052633 filed Feb. 11, 2013. This application is based upon and claims the benefit of priority to German Application No. 10 2012 202 779.3 filed on Feb. 23, 2012.

The present invention relates to a process for preparing a product mixture by industrial hydroformylation of an isobutene-containing hydrocarbon stream and for separating the resulting product mixture, and to an apparatus for the process according to the invention and to the use of an inventive apparatus.

Hydroformylation is generally understood in the industrial sector to mean the reaction of an olefin with synthesis gas (gas mixture consisting principally of carbon monoxide and hydrogen), usually under pressure and in the presence of a transition metal complex catalyst, to give an aldehyde extended by one carbon atom compared to the olefin.

Basic introductions to hydroformylation are given by: Falbe, Jürgen: New Syntheses with Carbon Monoxide. Springer Verlag 1980, Berlin, Heidelberg, New York and Pruett, Roy L.: Hydroformylation. Advances in Organometallic Chemistry Vol. 17, Pages 1-60, 1979.

In general, hydroformylation serves to prepare higher aldehydes. Higher aldehydes, especially those having 3 to 25 carbon atoms, are utilized, for example, as synthesis precursors for preparation of carboxylic acids and as fragrances. They are often converted industrially by catalytic hydrogenation to the corresponding alcohols, which serve in turn for the production of plasticizers and detergents. Owing to the significance of the hydroformylation products for major industry, the oxo process is performed on the industrial scale.

Hydroformylation of the $C_4$-olefin isobutene forms isovaleraldehyde, which is referred to hereinafter as 3-methylbutanal or 3 MBA for short. 3 MBA is used for production of fragrances and aromas, and as synthesis precursor.

In industrial scale hydroformylation, organophosphorus metal complex catalysts based on cobalt or rhodium are nowadays used. The catalysts are dissolved homogeneously in the liquid hydroformylation mixture. In the course of separation of the target product (of the aldehydes) from the hydroformylation mixture, the homogeneous catalyst also has to be removed gently from the hydroformylation mixture, since the complex catalyst is comparatively sensitive to changes in state and could lose its activity. Traditionally, the catalyst is separated by distillation from the hydroformylation mixture. In order to lower the risk of deactivation and to lower the energy consumption of the process, there have recently been efforts to separate the homogeneously dissolved catalyst from the hydroformylation mixture with the aid of membrane technology (nanofiltration).

The basics of membrane-supported organophilic nanofiltration for separation of homogeneously dissolved catalyst complexes from hydroformylation mixtures are described by Priske, M. et al.: Reaction integrated separation of homogeneous catalysts in the hydroformylation of higher olefins by means of organophilic nanofiltration. Journal of Membrane Science, Volume 360, Issues 1-2, 15 Sep. 2010, Pages 77-83; doi:10.1016/j.memsci.2010.05.002.

EP1931472B1 too is concerned generally with organophilic nanofiltration for separation of homogeneously dissolved catalyst complexes from hydroformylation mixtures.

A process for preparing 3-methylbutanal by hydroformylation of isobutene is described in the patent application WO2008006633.

The catalyzed hydroformylation of olefins to the corresponding aldehydes is effected typically in homogeneous liquid phase, which means that catalyst, olefin and products are in one phase, the transition metal complex catalyst being dissolved homogeneously in the liquid reaction mixture which also comprises the olefin to be hydroformylated and products of the hydroformylation. Products formed in the hydroformylation are, as well as said aldehyde, 3-methylbutanal, as the primary product, typically also higher-boiling conversion products (typically referred to as high boilers). In addition, an inert solvent for the transition metal complex catalyst, for example dioctyl phthalate or diisononyl phthalate or isononyl benzoate or mixtures thereof, may be present in the reaction mixture.

"High boilers" are understood here to mean substances which boil at a higher temperature and have higher molar masses than the primary hydroformylation product (aldehyde having one carbon atom more than the olefin used) and the alcohol obtained therefrom by hydrogenation. High boilers form through conversion reactions from the primary hydroformylation product. The high boilers typically formed in industrial hydroformylations include aldolization products and acetalization products, and also esters which form through reaction of alcohols and acids, the alcohols and acids being formed particularly through disproportionation of aldehydes.

The industrial hydroformylation of isobutene typically gives rise to a product mixture which, as well as the primary 3-methylbutanal product which is the target product of the industrial hydroformylation of isobutene, comprises conversion products in the form of high boilers and the transition metal complex catalyst and the free ligands thereof. According to the conversion performance of the reaction, the product mixture withdrawn from the reactor may also comprise unconverted reactant, i.e. isobutene, hydrogen or carbon monoxide. In order to increase the purity of the primary 3-methylbutanal product and to recover the transition metal complex catalyst, it is necessary to separate the 3 MBA, conversion product and catalyst constituents and any unconverted feed stocks in the product mixture obtained in the hydroformylation from one another.

A process for enriching a homogeneous catalyst from a process stream is known from WO02010097376A1. The process stream originates, for example, from a process for hydroformylation of olefins, preferably having 2 to 25 carbon atoms, to the corresponding aldehydes, especially isononanal and isotridecanal. The homogeneous catalyst from the process stream is enriched by conducting the process stream through at least one nanofiltration membrane consisting entirely or partly of a polymer having planar polymer units joined to one another via a rigid linker, the linker having an internal twist such that at least one planar polymer unit is bonded via the linker in a non-coplanar arrangement with at least one second planar polymer unit. In the membrane filtration, the catalyst system remains in the retentate, while the high boilers are removed with the permeate. The separation by membrane filtration is preferably preceded by a distillative separation of the output from the hydroformylation reactor into a distillate comprising unconverted olefins and the desired aldehydes, and a bottom product comprising high boilers and the catalyst system.

Another process for separating and partly recycling a transition metal complex catalyst from a reaction mixture, for example from the reaction mixture obtained in an industrial hydroformylation, is known from WO2010097428. This process is based on a combination of an at least one-stage membrane separation and an adsorption. This involves separating a catalyst-containing stream by means of at least one one-stage membrane separation step into a transition metal complex catalyst-enriched retentate stream and a transition metal complex catalyst-depleted permeate stream. The transition metal complex catalyst-enriched retentate stream is recycled into the reactor. The transition metal complex catalyst-depleted permeate stream is sent to an adsorption step in which further separation of the transition metal complex catalyst from the permeate stream is affected.

The aim of these and other processes known from the prior art is to separate the transition metal complex catalyst as far as possible from the high boilers in order to achieve maximum recovery of the transition metal complex catalyst. The catalyst removed can—optionally after required workup—be recycled into the hydroformylation reactor, such that the economic viability of the process can be improved.

The formation of high boilers reduces the yield of the hydroformylation in relation to the primary 3-methylbutanal product and therefore impairs the economic viability of the process. In the interests of improved exploitation of the raw materials used (isobutene; synthesis gas) and of the transition metal complex catalyst used, it is therefore desirable to minimize the proportion of high boilers in the product mixture.

The problem addressed by the present invention is thus that of specifying a process and an apparatus for preparation of a product mixture by industrial hydroformylation of an isobutene-containing hydrocarbon stream and for separation of the resulting product mixture, which enable minimization of the proportion of high boilers in the product mixture and hence enhancement of the yield of the reaction.

This problem is solved by a process according to the invention for preparing a product mixture by industrial hydroformylation of an isobutene-containing hydrocarbon stream and for separating the resulting product mixture, comprising the following steps:
  a) hydroformylating the isobutene-containing hydrocarbon stream in a hydroformylation reactor in the presence of a transition metal complex catalyst, so as to obtain a product mixture comprising at least 3-methylbutanal, conversion products in the form of high boilers and 3-methylbutanoic acid, and the transition metal complex catalyst along with the free ligands thereof,
  b) separating the product mixture by means of a nanofiltration device comprising one or more membrane separation stages, such that the transition metal complex catalyst and the free ligands thereof are enriched in the resulting retentate of the nanofiltration device with respect to 3-methylbutanal and 3-methylbutanoic acid, and such that 3-methylbutanal and 3-methylbutanoic acid are each enriched in the resulting permeate of the nanofiltration device with respect to the transition metal complex catalyst, the concentration of the 3-methylbutanoic acid being lower in the resulting retentate than in the permeate,
  c) separating the resulting permeate of the nanofiltration device by means of a thermal separating device comprising one or more separation stages into at least one first fraction and a second fraction, the first fraction having a higher concentration of 3-methylbutanal than the second fraction and a lower concentration of conversion products in the form of high boilers and 3-methylbutanoic acid than the second fraction,
  d) recycling at least a substream of the resulting retentate of the nanofiltration device into the hydroformylation reactor.

To solve the stated problem, it was first necessary to identify the individual species involved in the formation of the high boilers and to elucidate the kinetics of the reactions involved. In in-house studies for elucidation of the kinetics of the formation of high boilers in the hydroformylation of isobutene to 3-methylbutanal, it was found that, surprisingly, 3-methylbutanoic acid formed as an oxidation product of 3-methylbutanal plays a critical role in the formation of high boilers. The formation of high boilers begins with the aldol condensation of 3-methylbutanal:

The aldol condensate can be reduced by reaction with the primary 3-methylbutanal product to give a dihydric $C_{10}$-alcohol, the primary 3-methylbutanal product being oxidized to 3-methylbutanoic acid:

Esterification of the $C_{10}$-alcohol with 3-methylbutanoic acid then forms $C_{15}$ high boilers in a Tishchenko reaction:

Further esterification of the $C_{15}$ high boiler with 3-methylbutanoic acid can finally also form a $C_{20}$ high boiler:

Thus, the $C_{15}$ and $C_{20}$ high boilers are formed to a crucial degree substantially via reactions involving 3-methylbutanoic acid. 3-Methylbutanoic acid is occasionally abbreviated hereinafter to 3 MBAc.

This finding is the basis of the present invention: the inventive solution to the above-mentioned problem of minimizing the proportion of high boilers in the resulting product mixture of the hydroformylation primarily involves separating 3-methylbutanoic acid very substantially from the transition metal complex catalyst to be recycled into the hydroformylation reactor. This can be achieved by, in the step of separating the resulting product mixture from the hydroformylation, enriching the transition metal complex catalyst which is to be recycled into the hydroformylation reactor in the resulting retentate of the nanofiltration device, while the conversion products of the hydroformylation reaction, especially 3 MBAc, are enriched in the resulting permeate of the nanofiltration device. It has been found that, surprisingly, substantial removal of the 3-methylbutanoic acid from the transition metal complex catalyst can be achieved by means of nanofiltration, i.e. separation of the resulting product mixture of the hydroformylation using one or more nanofiltration membranes. For this purpose, for the nanofiltration separation step of the process according to the invention, a nanofiltration device comprising one or more nanofiltration membranes is used, this featuring a particularly low retention for 3-methylbutanoic acid. The retention of the nanofiltration membrane for 3-methylbutanoic acid is preferably −1 or less, more preferably −5 or less and especially preferably −10 or less. The definition of the retention of a membrane can be found further down.

By virtue of the separation thereof from the transition metal complex catalyst which is to be recycled into the hydroformylation reactor, the 3-methylbutanoic acid discharged with the permeate of the nanofiltration device is no longer available in the reactor as a reactant for high boiler formation, and so important reactions involved in high boiler formation proceed only to a lower degree, if at all. Thus, the loss is reduced based on the primary 3-methylbutanal product.

An important aspect of the inventive teaching thus consists in the use of a nanofiltration device for separation of the catalyst complex from the product mixture, this having a particularly high permeability for 3-methylbutanoic acid.

A "nanofiltration device" in the context of this invention is understood to mean a separation apparatus which accomplishes its separation task exclusively with the aid of membranes, at least one of the membranes being a nanofiltration membrane. The nanofiltration device may comprise one or more membrane separation stages; accordingly, the nanofiltration device may work in one or more stages. Each membrane separation stage has three connections, a feed and two outlets, namely retentate and permeate. The constituents of the feed which pass through the membrane accumulate in the permeate, while the substances which are retained by the membrane accumulate in the retentate. The resulting permeate and the resulting retentate are understood to mean the two outputs of a nanofiltration device at the interfaces thereof with the other components of the apparatus for performance of the process according to the invention. If the nanofiltration device works with only one stage, and therefore has only one membrane separation stage, the resulting permeate or the resulting retentate of the nanofiltration device corresponds to the permeate or the retentate of the sole membrane separation stage.

The basic knowledge of the person skilled in the art in the field of membrane filtration is described in Melin/Rautenbach: Membranverfahren. Grundlagen der Modul- und Anlagenauslegung. [Membrane processes. Basics of module and system design.] Springer, Berlin Heidelberg 2004.

Nanofiltration is a pressure-driven membrane separation process. The separation limit (molecular weight cut-off, MWCO; cf. Y. H. See Toh, X. X. Loh, A. Bismarck, A. G. Livingston, In search of a standard method for the characterisation of organic solvent nanofiltration membranes, J. Membr. Sci, 291 (2007)120-1251) is in the range from 150 g/mol to 2000 g/mol.

This value can be used to delimit nanofiltration from other membrane separation processes such as microfiltration and ultrafiltration. The separation limit is defined as the molar mass of a preferably inert indicator system (for example polystyrene standards or alkane standards in Toh, Loh, Bismarck and Livingston) at which a membrane has a retention of 90%. The exact separation limit of a nanofiltration membrane is determined by the membrane used and the respective solvent, and by the process conditions such as pressure and temperature. In nanofiltration, impervious or porous membranes are used. Nanofiltration membranes feature low retention for low molecular weight organic substances.

The retention R of a membrane is determined by the local concentrations of a component i of the non-permeating stream (retentate) and of the stream permeating through the membrane (permeate). If retentate and permeate have ideal mixing along the membrane, the local retentate and permeate concentrations correspond to the respective concentrations of the retentate and permeate obtained overall. The retention R of a membrane for a component i present in the stream supplied is defined as follows:

$$R = 1 - c_{Pi}/c_{Ri}$$

In this formula, $c_{Pi}$ is the concentration of component i in the permeate P and $c_{Ri}$ is the concentration of component i in the retentate R. In the boundary case of full retention of component i by the membrane, $c_{Pi}=0$ and $R=1$. In the case of preferred permeation of component i, $c_{Pi}>c_{Ri}$, and $R<0$.

Preferably, the nanofiltration device for use in the process according to the invention comprises one or more nanofiltration membranes, the or at least one of the nanofiltration membranes having a retention for 3-methylbutanoic acid of −1 or less, more preferably −5 or less and especially −10 or less. Thus, it is possible to achieve substantial discharge of the 3-methylbutanoic acid from the resulting product mixture of the hydroformylation which is supplied as feed to the nanofiltration device.

Membranes which appear suitable for the separation task are those which have a separation-active layer of a material selected from cellulose acetate, cellulose triacetate, cellulose nitrate, regenerated cellulose, polyimides, polyamides, polyetheretherketones, sulphonated polyetheretherketones, aromatic polyamides, polyamidimides, polybenzimidazoles, polybenzimidazolones, polyacrylonitrile, polyarylethersulphones, polyesters, polycarbonates, polytetrafluoroethylene, polyvinylidene fluoride, polypropylene, polydimethylsiloxane, silicones, polyphosphazenes, polyphenylsulphides, polybenzimidazoles, nylon-6,6, polysulphones, polyanilines, polyurethanes, acrylonitrile/glycidyl methacrylate (PANGMA), polytrimethylsilylpropyne, polymethylpentyne, polyvinyltrimethylsilane, alpha-aluminas, titanias, gamma-aluminas, polyphenylene oxide, silicas, zirconias, ceramic membranes hydrophobized with silanes, as described in DE10308111. Polymers with intrinsic microporosity (PIM) such as PIM-1 and others, as described, for example, in EP0781166 and in "Membranes" by I. Cabasso, Encyclopedia of Polymer Science and Technology, John Wiley and Sons, New York, 1987. The above-mentioned substances may especially be present in crosslinked form in the separation-active layer, optionally through addition of assistants, or as what are called mixed matrix membranes with fillers, for example carbon nanotubes, metal-organic frameworks or hollow spheres, and particles of inorganic oxides or inorganic fibres, for example ceramic or glass fibres.

Preference is given to using membranes which have, as the separation-active layer, a polymer layer of polydimethylsiloxane, polyimide, polyamidimide, acrylonitrile/glycidyl methacrylate (PANGMA), polyamide or polyetheretherketone, which are formed from polymers with intrinsic microporosity (PIM) such as PIM-1, or wherein the separation-active layer is formed by means of a hydrophobized ceramic membrane. Very particular preference is given to using membranes composed of silicones or polyamidimide. Such membranes are commercially available.

In in-house studies, it has been found that nanofiltration membranes comprising one or more polymers containing imide groups or consisting of one or more polymers containing imide groups are particularly suitable for the discharge of 3-methylbutanoic acid from the product mixture of the hydroformylation which is supplied as feed to the nanofiltration device. Representatives of this membrane class are especially membranes of polyimide or polyamidimide. For example, it is possible to use the thermoplastic polyimide which is obtainable under the Matrimid® brand name from Huntsman Advanced Materials GmbH, Basel (Switzerland). Nanofiltration membranes composed of polyimide or polyamidimide feature particularly low retention for 3-methylbutanoic acid. Preference is therefore given to using, in the nanofiltration device, one or more nanofiltration membranes comprising or consisting of one or more polymers containing imide groups, the polymer(s) containing imide groups being selected such that the retention of the nanofiltration membrane for 3-methylbutanoic acid is −1 or less, preferably −5 or less and more preferably −10 or less. Nanofiltration membranes containing imide groups are commercially available, for example under the STARMEM® 122 and 240 product names from W. R. Grace & Co.-Conn. 7500 Grace Drive Columbia, Md. 21044 US, or membranes of the Puramem® and Duramem® product families obtainable from Evonik Industries AG, Essen (Germany). Puramem® and Duramem® contain polyimides such as P84 and/or Matrimid 5218.

The nanofiltration device for use in the process according to the invention more preferably comprises one or more nanofiltration membranes, the or at least one of the nanofiltration membranes having a separation limit in the range from 150 to 2000 g/mol, preferably 200 to 600 g/mol, more preferably 350 to 500. Since retention of 3-methylbutanoic acid is unwanted in the process according to the invention, preference is given in accordance with the invention to using a nanofiltration membrane whose separation limit is higher than the molar mass of 3-methylbutanoic acid (102 g/mol). Since the high boilers are not to be retained in the retentate either, the separation limit thereof is preferably above the molar mass of the high boilers (200 to 350 g/mol) but below that of the catalyst (500 to 1000 g/mol).

Very particular preference is given to using, in a nanofiltration device for use in the process according to the invention, one or more nanofiltration membranes comprising or consisting of one or more polymers containing imide groups, the polymer(s) containing imide groups being selected such that the separation limit of the nanofiltration membrane is in the range from 150 to 2000 g/mol.

Further parameters of relevance for the success of the separation step in the nanofiltration device are the temperature, the transmembrane pressure, the Reynolds number in the course of flow through the nanofiltration membrane, and the partial pressure of carbon monoxide and/or hydrogen. The step of separation of the product mixture obtained by hydroformylating the isobutenic hydrocarbon stream in the nanofiltration device is preferably performed at a temperature in the range from 10 to 150° C. and/or at a transmembrane pressure in the range from 0.5 to 6 MPa and/or at a Reynolds number between 55 and 13 500, preferably between 100 and 3500 and most preferably between 170 and 900, and/or in the presence of carbon monoxide and/or hydrogen, preferably at a partial carbon monoxide pressure of at least 200 kPa in the feed, in the retentate and in the permeate.

Prior to entry into the nanofiltration device, the resulting reaction mixture leaving the hydroformylation reactor is preferably first cooled, if necessary for reasons of membrane stability or for the establishment of the separation limit, and decompressed, preferably to a pressure exceeding 200 kPa. In the course of this, volatile constituents such as unconverted isobutene or hydrogen and carbon monoxide are partly removed and optionally recycled. The synthesis gas which remains under the decompression pressure is used to supply the product mixture comprising the primary 3-methylbutanal product, conversion products in the form of high boilers and 3-methylbutanoic acid and the transition metal complex catalyst and the free ligands thereof and any unconverted product to a high-pressure membrane pump which generates the transmembrane pressure needed for the nanofiltration process. Optionally, the high-pressure pump may be proceeded upstream by a preliminary filter system.

The transmembrane pressure is understood to mean the pressure difference between the feed side and the permeate side of the nanofiltration membrane per separation stage. This pressure difference is the primary driving force of the membrane filtration.

In order to avoid a concentration excess (concentration polarization) or else the formation of deposits on the nanofiltration membrane (membrane fouling), certain flow conditions have to be maintained in the course of separation in the nanofiltration device. It has been found that the concentration excess and the formation of deposits from a stream flowing through a nanofiltration membrane depend on the turbulence thereof and hence on the Reynolds number thereof. Thus, irrespective of the design of the membrane module, it should be ensured that the Reynolds number is between 55 and 13 500, preferably between 100 and 3500 and most preferably between 170 and 900. This is especially true of systems having a kinematic viscosity less than 10 mPa·s. Under these flow conditions, concentration excess and deposits are reduced to a reasonable degree.

The dimensionless Reynolds number Re is defined as $Re = w \, d_h / v$, where v describes the kinematic viscosity, w the mean through-flow rate of the membrane and $d_h$ the hydraulic diameter as the characteristic length of the membrane module.

The nanofiltration device may comprise a multitude of separation stages in the form of membrane modules (connected in series or parallel), the respective permeate obtained after each separation stage being supplied as feed to the next separation stage, and the permeate from the last separation stage being supplied to the thermal separation. Each separation stage comprises at least one membrane module, each membrane module comprising an individual or more than one nanofiltration membrane. A membrane module is understood by the person skilled in the art to mean a practically manageable use-specific arrangement of the membrane in an assembly.

The step of thermal separation of the permeate, which follows the step of separation in a nanofiltration system in the process according to the invention, typically comprises a distillation or thin-film evaporator or falling-film evaporator or a combination thereof, in which the first fraction is obtained as the top product and the second fraction as the bottom product. Preferably, after the step of thermal separation, no further separation of the second fraction from the thermal separation by means of a nanofiltration device is required. A further separation of the second fraction obtained as the bottom product is dispensable especially when the transition metal complex catalyst is already retained in the retentate in the prior separation of the product mixture which is the result of the hydroformylation in the nanofiltration device to such a high degree that only such a small amount of catalyst is present in the permeate that the cost and inconvenience of recovery from the high-boiling (second) fraction of the thermal separation is uneconomic.

In order to solve the above-mentioned problem, it is additionally advantageous to conduct the industrial hydroformylation in such a way that the further reactions which lead to the formation of 3-methylbutanoic acid and high boilers proceed only to a minimum degree. This can be achieved by a suitable setting of one or more process parameters, especially from the group consisting of pressure, temperature, mean residence time of the reaction mixture in the hydroformylation reactor, composition of the synthesis gas, concentration of the transition metal and transition metal/ligand ratio of the transition metal complex catalyst.

"Reaction mixture" is understood to mean the overall mixture present in the hydroformylation reactor comprising the reactants (isobutene and synthesis gas), the primary product of the hydroformylation (3-methylbutanal), conversion products formed therefrom (3-methylbutanoic acid and high boilers) and the transition metal complex catalyst. By hydroformylation of the isobutene reactant, optionally after removal of unconverted isobutene, the resulting product mixture to be separated by nanofiltration is obtained from this reaction mixture, comprising at least 3-methylbutanal, conversion products in the form of high boilers and 3-methylbutanoic acid, and the transition metal complex catalyst and the free ligands thereof. If unconverted reactants (isobutene, hydrogen, carbon monoxide) are not separated from the reactor output upstream of the nanofiltration device, these are part of the product mixture which has been run into the feed of the nanofiltration device. In principle, full conversion of the isobutene is desirable, but cannot always be achieved in industrial practice. Typical conversion rates exceed 95% by weight. Unconverted isobutene may be removed immediately upstream of the nanofiltration device in order that the feed thereof is virtually isobutene-free. Alternatively, it is possible to allow remaining isobutene to permeate through the membranes and to remove it in the course of the thermal removal of the 3 MBA target product which is required in any case, and to return it to the hydroformylation reactor. This variant is preferable since thermal separation processes damage the catalyst complex. The carbon monoxide reactant should, however, preferably also be present in the feed, permeate and retentate of the nanofiltration device in order to stabilize the catalyst complex.

In an advantageous development of the process according to the invention, one or more process parameters in the step of hydroformylating the isobutenic hydrocarbon stream are set such that the total concentration of conversion products in the form of high boilers and 3-methylbutanoic acid, based on the weight of the product mixture, i.e. the reactor output, is 30% by weight or less, the parameter(s) to be set preferably being selected from the group consisting of pressure, temperature, mean residence time of the reaction mixture in the hydroformylation reactor, composition of the synthesis gas, concentration of the transition metal and transition metal-ligand ratio of the transition metal complex catalyst.

A reduction in the mean residence time of the reaction mixture in the hydroformylation reactor makes it possible to reduce the time available for the unwanted conversion reactions, but the mean residence time, on the other hand, must be sufficiently high to allow an economically viable degree of conversion of the reactants. The mean residence time can be influenced, for example, by the design of the length of the reactor.

A reduction in the temperature in the hydroformylation reactor can reduce the rate of the unwanted conversion reactions, but the temperature, on the other hand, must be sufficiently high to allow an economically viable degree of conversion of the reactants.

Preference is given to setting one or more process parameters, especially the temperature and/or the mean residence time, in the step of hydroformylating the isobutenic hydrocarbon stream such that the concentration of 3-methylbutanoic acid in the product mixture to be supplied to the nanofiltration device is in the range between 0.004 and 0.1% by weight, preferably in the range between 0.004 and 0.03% by weight.

The concentration of the catalyst complex in the resulting permeate is preferably 0.03% by weight or less.

According to the invention, the step of hydroformylating the isobutenic hydrocarbon stream is preferably performed
at a pressure in the range from 0.2 to 8 MPa,
and/or
at a temperature in the range from 70 to 130° C.
and/or
with a mean residence time of the reaction mixture in the hydroformylation reactor in the range from 1 to 4 hours
and/or
a synthesis gas composition (CO:$H_2$) of 1:3 to 3:1
and/or
a transition metal concentration in the range from 10 to 100 ppm is the hydroformylation reactor
and/or
a transition metal/ligand ratio in the range from 1:4 to 1:50.

In the hydroformylation step of the process according to the invention, preference is given to using a transition metal complex catalyst whose transition metal is rhodium and/or whose ligand(s) is/are selected from the group of the organophosphorus ligands. It is also possible to use a transition metal complex catalyst whose transition metal is cobalt.

In in-house studies, it has been found that, at temperatures from 130° C. in the hydroformylation reactor, the formation of 3-methylbutanoic acid and high boilers formed therefrom increases significantly. It is therefore preferable in accordance with the invention that the temperature in the hydroformylation reactor does not exceed 130° C. Preference is given to performing the hydroformylation at a temperature in the range from 80 to 110° C. Irrespective of this, individual process parameters or all further process parameters mentioned above can be optimized to the effect that the formation of 3-methylbutanoic acid and high boilers is restricted.

Preferably, in a process according to the invention for preparing a product mixture by industrial hydroformylation of an isobutene-containing hydrocarbon stream and for separation of the resulting product mixture, individual or all features of the variants emphasized above as particularly preferred are combined with one another in order to achieve optimal separation of 3-methylbutanoic acid from the transition metal complex catalyst to be recycled into the reactor, combined with low formation of 3-methylbutanoic acid and high boilers. Therefore, a preferred process according to the invention comprises the steps of hydroformylating an isobutenic hydrocarbon stream in the presence of a rhodium complex catalyst having one or more organophosphorus ligands at a pressure in the range from 0.2 to 8 MPa and a temperature in the range from 70 to 130° C. with a mean residence time in the range from 1 to 4 h, a synthesis gas composition CO:$H_2$ of 1:3 to 3:1, a rhodium concentration in the reactor in the range from 10 to 100 ppm and a rhodium/ligand ratio in the range from 1:4 to 1:50;

separating the resulting product mixture of the hydroformylation by means of a nanofiltration device at a temperature in the range from 10 to 150° C., a transmembrane pressure in the range from 0.5 to 6 MPa, at a Reynolds number between 170 and 900, and a partial carbon monoxide pressure of greater than 0.2 MPa into feed, retentate and permeate of each membrane separation stage;

thermally separating the resulting permeate of the nanofiltration device by means of distillation into a first fraction and a second fraction, the first fraction containing a higher concentration of 3-methylbutanal than the second fraction and a lower concentration of high boilers than the second fraction, recycling at least a substream of the resulting retentate of the nanofiltration device into the hydroformylation reactor.

In order to solve the above-mentioned problem, it is additionally advantageous to monitor the concentration of 3-methylbutanoic acid formed in one or more streams (especially in the feed stream, permeate stream and retentate stream) of the process according to the invention, and to take suitable counter-measures on exceedance of fixed maximum values.

An advantageous further development of the process according to the invention therefore comprises the step of
monitoring the concentration of 3-methylbutanoic acid in the retentate of the nanofiltration device, and preferably also in the resulting product mixture of the hydroformylation and/or in the feed of the nanofiltration device and/or in the permeate of the nanofiltration device.

Suitable methods for monitoring the concentration of 3-methylbutanoic acid in the retentate of the nanofiltration device, and preferably also in the resulting product mixture of the hydroformylation and/or in the feed and/or in the permeate of the nanofiltration device, comprise a measurement of the concentration of 3-methylbutanoic acid in the respective process stream with a measurement method selected from the group consisting of gas chromatography. By monitoring the concentration of 3-methylbutanoic acid in the retentate of the nanofiltration device, it is possible to check how high the amount of 3-methylbutanoic acid is which is recycled into the hydroformylation catalyst with the transition metal complex catalyst enriched in the retentate of the nanofiltration. A rise in the concentration of 3-methylbutanoic acid in the retentate of the nanofiltration device could indicate blockage of the nanofiltration membrane by deposits (membrane fouling). In a preferred variant of the process according to the invention, on exceedance of a fixed maximum concentration of the 3-methylbutanoic acid in the retentate of the nanofiltration device, the recycling of the retentate into the hydroformylation reactor is stopped. This prevents the concentration of 3-methylbutanoic acid from rising in the hydroformylation reactor, thus promoting the unwanted formation of high boilers.

In a particularly preferred variant of the process according to the invention, exceedance of a fixed maximum concentration of 3-methylbutanoic acid in the retentate of the nanofiltration device additionally initiates a check of the function of the nanofiltration device and, if necessary, an exchange or regeneration of one or more nanofiltration membranes. Such a measure could be appropriate especially if the likewise monitored concentration of 3-methylbutanoic acid in the permeate simultaneously falls below a particular minimum value (see below).

By monitoring the concentration of 3-methylbutanoic acid in the feed of the nanofiltration device or in the resulting product mixture of the hydroformylation, it is possible to check how high the amount of 3-methylbutanoic acid is in the product mixture which is obtained by hydroformylating the isobutenic hydrocarbon stream and which is supplied as feed to the nanofiltration device, preferably after decompression with removal of unconverted isobutene and optionally also preliminary filtration. An excessively high concentration of 3-methylbutanoic acid in the feed of the nanofiltration device is an indication of process parameters not set optimally with regard to the formation of high boilers in the industrial hydroformylation in the hydroformylation reactor. A sudden rise in the concentration of 3-methylbutanoic acid in the feed of the nanofiltration device could even be an indication of failure or out-of-control regulation of one or more process parameters in the hydroformylation. Thus, this described variant of the process according to the invention can contribute to reliable monitoring of the process parameters of the hydroformylation, and may even contribute to avoidance of incorrect production and disrupted operation.

In a preferred variant of the process according to the invention, on exceedance of a fixed maximum concentration of 3-methylbutanoic acid in the feed of the nanofiltration device, one or more process parameters in the step of hydroformylating the isobutenic hydrocarbon stream in the hydroformylation reactor are modified such that the concentration of 3-methylbutanoic acid in the feed of the nanofiltration device is lowered to or below the fixed maximum. The suitable setting of one or more process parameters of the hydroformylation is preferably effected as described above, the parameters to be set being selected especially from the group consisting of pressure, temperature, mean residence time of the reaction mixture in the hydroformylation reactor, composition of the synthesis gas, concentration of the transition metal and transition metal/ligand ratio of the transition metal complex catalyst.

By monitoring the concentration of 3-methylbutanoic acid in the permeate of the nanofiltration device, it is possible to check how high the amount of 3-methylbutanoic acid is which permeates through the one or more nanofiltration membranes of the nanofiltration plant. This allows the proper operation of the nanofiltration device to be monitored. A decline in the concentration of 3-methylbutanoic acid in the permeate of the nanofiltration device could indicate blockage of the nanofiltration membrane by deposits (membrane fouling). In a preferred variant of the process according to the invention, when the concentration of 3-methylbutanoic acid in the permeate of the nanofiltration device goes below a fixed minimum, a check of the function of the nanofiltration device is initiated and, if necessary, an exchange or regeneration of one or more nanofiltration membranes.

Preferably, in a process according to the invention for preparing a product mixture by industrial hydroformylation of an isobutene-containing hydrocarbon stream and for separation of the resulting product mixture, individual or all features of the developments and variants emphasized above as particularly preferred are combined with one another, in order to achieve an optimal separation of 3-methylbutanoic acid from the transition metal complex catalyst to be recycled into the reactor and low formation of 3-methylbutanoic acid and high boilers in the hydroformylation and comprehensive monitoring of the concentration of 3-methylbutanoic acid in all relevant streams in the process according to the invention.

The present invention relates additionally to an apparatus for the performance of the process according to the invention, especially for the above-described preferred variants of the process according to the invention. An apparatus for performance of the process according to the invention comprises:

a hydroformylation reactor (R) for hydroformylation of an isobutenic hydrocarbon stream (1) in the presence of a transition metal complex catalyst, a nanofiltration device (M) comprising one or more membrane separation stages for separation of the product mixture (2) formed in the hydroformylation reactor (R), such that the transition metal complex catalyst and the free ligands thereof are enriched in the resulting retentate (3) of the nanofiltration device (M) with respect to 3-methylbutanal and 3-methylbutanoic acid, and 3-methylbutanal and 3-methylbutanoic acid are enriched in the resulting permeate of the nanofiltration device (M) with respect to the transition metal complex catalyst, such that the concentration of 3-methylbutanoic acid in the resulting retentate (3) is lower than in the resulting permeate (4), the nanofiltration device (M) comprising one or more nanofiltration membranes, the or at least one of the nanofiltration membranes having a retention for 3-methylbutanoic acid of −1 or less, more preferably −5 or less, and especially −10 or less, at least one thermal separation device (D) for thermal separation of the resulting permeate (4) of the nanofiltration device (M) into a first fraction (5) and a second fraction (6), the first fraction (5) having a higher concentration of 3-methylbutanal than the second fraction (6) and a lower concentration of conversion products in the form of high boilers and 3-methylbutanoic acid than the second fraction (6), means for recycling at least a substream of the resulting retentate (3) of the nanofiltration device (M) into the hydroformylation reactor (R).

The apparatus for performance of the process according to the invention may also comprise constituents customary in the prior art, for example pumps, customary metering, measurement, control and regulation devices, heating and cooling apparatuses etc. Such constituents of apparatuses for industrial synthesis and separation processes are known to those skilled in the art, these constituents forming part of the prior art and being customary in chemical process technology.

The hydroformylation reactor used is preferably an apparatus from the group consisting of stirred tank, bubble column, jet nozzle reactor, tubular reactor and loop reactor, and the apparatus may be provided with internals.

In a particularly preferred embodiment, the hydroformylation reactor takes the form of a bubble column reactor. In this inventive apparatus, the length dimension of the hydroformylation reactor is preferably selected so as to result in a residence time of the reaction mixture in the hydroformylation reactor which is sufficient for an economically viable degree of conversion of the reactants to the primary 3-methylbutanal hydroformylation product but does not allow the high degree of conversion of the primary 3-methylbutanal hydroformylation product to conversion products in the form of 3-methylbutanoic acid and high boilers.

The nanofiltration device of the inventive apparatus preferably comprises one or more membrane modules. In these modules, the nanofiltration membranes are arranged such that the flow over the retentate side of the nanofiltration membrane may be such as to counteract the concentration polarization of the components removed, i.e. of the transition metal complex catalyst, and also to impose the necessary driving force (pressure). The permeate is combined in the permeate collecting space on the permeate side of the nanofiltration membrane and removed from the module. Standard membrane modules have the nanofiltration membranes in the form of membrane disks, membrane pads or membrane pockets. Particular preference is given to membrane modules with open-channel pad module systems in which the nanofiltration membranes are thermally welded or bonded to form membrane pockets or pads, or wound modules in which the nanofiltration membranes are bonded or welded to form membrane pockets or membrane pads and are wound with feed spacers around a permeate collecting tube.

Preferably, the nanofiltration device of the inventive apparatus is configured such that the above-described preferred process parameters, especially process parameters from the group consisting of pressure, temperature, mean residence time of the reaction mixture in the hydroformylation reactor, composition of the synthesis gas, concentration of the transition metal and transition metal/ligand ratio of the transition metal complex catalyst, can be established and/or the above-described preferred variants of the execution of the step of separation of the resulting product mixture of the hydroformylation can be implemented.

The nanofiltration device may comprise a multitude of separation stages arranged such that, after each separation stage, the permeate obtained is supplied in each case as feed to the next separation stage, and the permeate from the last separation stage is supplied to the thermal separation. Each separation stage may be designed as a membrane module or several membrane modules arranged in parallel. Each membrane module may comprise one or more nanofiltration membranes arranged in parallel.

With regard to the selection of one or more suitable nanofiltration membranes for the nanofiltration device of the inventive apparatus, the above remarks regarding the selection of one or more suitable nanofiltration membranes apply correspondingly to the process according to the invention.

The nanofiltration device preferably comprises one or more nanofiltration membranes, the or at least one of the nanofiltration membranes having a separation limit in the range from 150 to 2000 g/mol, preferably 200 to 600 g/mol and more preferably from 350 to 500 g/mol.

In a preferred embodiment adapted especially for an above-described preferred variant of the process according to the invention, the inventive apparatus additionally comprises an apparatus for determination of the concentration of 3-methylbutanoic acid in the retentate of the nanofiltration device, preferably additionally a device for determination of the concentration of 3-methylbutanoic acid in the resulting product mixture of the hydroformylation and/or in the feed of the nanofiltration device and/or a device for determination of the concentration of 3-methylbutanoic acid in the permeate of the nanofiltration device, or a device for taking of samples from the retentate of the nanofiltration device, preferably additionally a device for taking of samples from the resulting product mixture of the hydroformylation and/or from the feed of the nanofiltration device and/or a device for taking of samples from the permeate of the nanofiltration device.

The apparatus for determining the concentration of 3-methylbutanoic acid in the feed of the nanofiltration device is preferably selected from the group consisting of gas chromatographs. The same applies to the optional devices for determination of the concentration of 3-methylbutanoic acid in the retentate and/or permeate of the nanofiltration device.

If direct measurement of the concentration of 3-methylbutanoic acid in the resulting product mixture of the hydroformylation and/or feed and/or retentate and/or permeate of the nanofiltration device is impossible or too complex, apparatuses for taking samples from the resulting product mixture of the hydroformylation, or from the feed and/or retentate and/or permeate of the nanofiltration device may be provided. In the samples taken with this apparatus regularly, i.e. at particular times or at particular intervals, or as required, from the feed, retentate and/or permeate, the concentration of 3-methylbutanoic acid is determined, for example, in a process control laboratory.

With regard to the information obtainable from the monitoring of the concentration of 3-methylbutanoic acid in the resulting product mixture of the hydroformylation and/or feed, in the retentate and in the permeate of the nanofiltration device and the advantages achievable with this monitoring, the above remarks relating to the process according to the invention apply, comprising the step of monitoring the concentration of 3-methylbutanoic acid in the retentate of the nanofiltration device, and preferably also in the resulting product mixture of the hydroformylation and/or in the feed and/or in the permeate of the nanofiltration device.

The present invention further relates to the use of an inventive apparatus, especially in the preferred embodiments thereof, for preparation of a product mixture by industrial hydroformylation of an isobutene-containing hydrocarbon stream and for separation of the resulting product mixture, especially by a process according to one of the preferred variants of the above-described process according to the invention.

Further preferred embodiments of the invention are evident from the claims.

The invention is described in detail hereinafter with reference to a working example and the figures, these do not restrict the scope of protection of the claims. The figures show:

Figure 1:
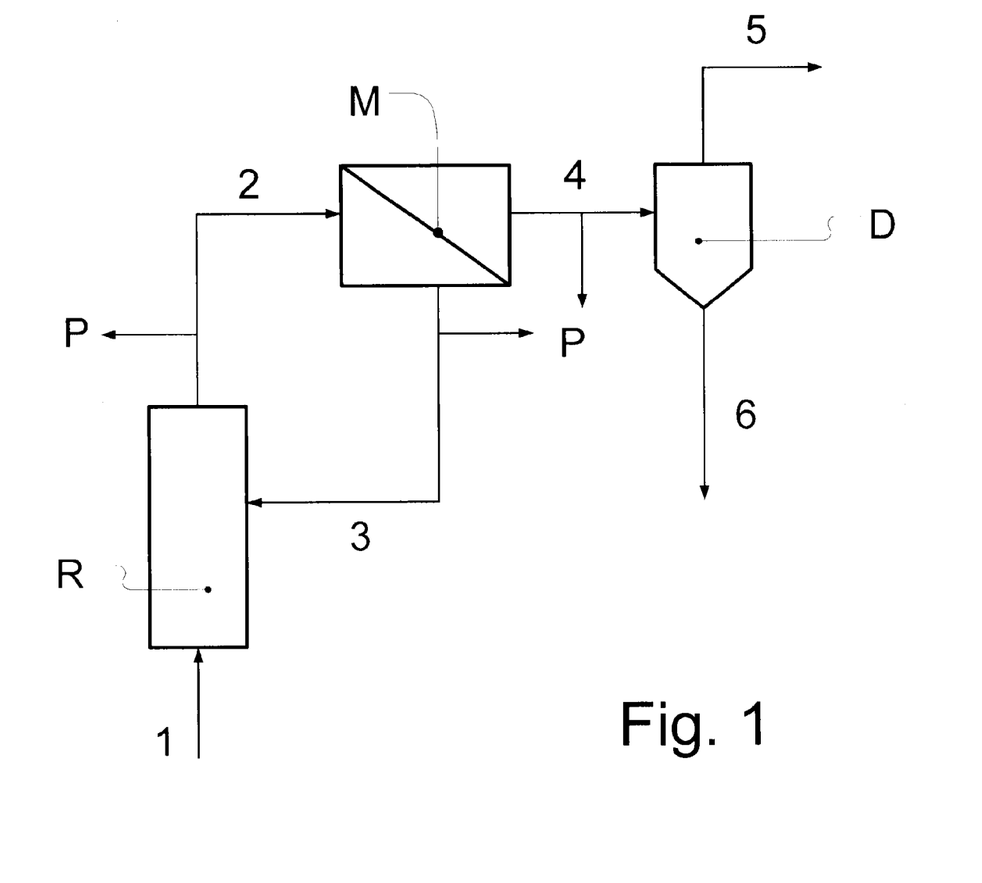
FIG. 1: apparatus for preparation of a product mixture by industrial hydroformylation of an isobutene-containing hydrocarbon stream and for separation of the resulting product mixture by the process according to the invention.

For preparation of a product mixture by industrial hydroformylation of an isobutene-containing hydrocarbon stream 1 and for separation of the resulting product mixture 2, an apparatus shown in FIG. 1 is used, comprising a hydroformylation reactor R in the form of a bubble column, a nanofiltration device M and a distillation device D. In the apparatus are provided sampling devices P which enable samples to be taken at particular intervals from the product stream 2 leaving the reactor R, and also from the retentate 3 and the permeate 4 of the nanofiltration device M.

The nanofiltration device M comprises a membrane module in the form of a wound module. The nanofiltration membrane is a membrane of the STARMEM 122 type from W. R. Grace & Co and comprises polyimide P84.

The hydroformylation reactor R is supplied with a hydrocarbon stream 1 comprising isobutene and synthesis gas, In the reactor R, the isobutene is hydroformylated to 3-methylbutanal at a pressure in the range from 0.2 to 8.0 MPa and a temperature in the range from 70 to 130° C. with a mean residence time in the range from 1 to 4 hours, a synthesis gas composition (CO/H2) of 1:3 to 3:1, a rhodium concentration in the range from 20 to 100 ppm and a rhodium/ligand ratio in the range from 1:4 to 1:50.

The resulting product mixture 2 of the hydroformylation, in which the concentration of 3-methylbutanoic acid is in the range between 0.01 and 0.04% by weight, is subsequently separated in a nanofiltration device M at a temperature in the range from 30 to 35° C., a transmembrane pressure in the range from 3.1 to 3.8 MPa and a partial carbon monoxide pressure in the range from 0.9 to 1.2 MPa. The nanofiltration device M is designed such that the Reynolds number is between 170 and 900 in the course of flow over the nanofiltration membrane.

A resulting retentate 3 and a resulting permeate 4 are withdrawn from the nanofiltration device M. The ratio of product mixture 2 supplied to the membrane—also referred to as feed—and permeate 4 was set to 0.82. The retentate stream 3 in which the transition metal complex catalyst is enriched is recycled into the reactor R.

Samples are taken with sampling apparatuses P at regular intervals from the product mixture 2 leaving the reactor R, the retentate 3 and the permeate 4, in order to determine the concentration of 3-methylbutanoic acid in the respective stream.

The resulting permeate 4 of the nanofiltration device M, in which the primary 3-methylbutanal hydroformylation product and 3-methylbutanoic acid are enriched, is separated by means of distillation in a thermal separation device in the form of a distillation plant D into a first fraction 5 and a second fraction 6. In the first fraction 5, which is obtained as the top product, the concentration of 3-methylbutanal is higher than in the second fraction 6, and the concentration of 3-methylbutanoic acid and high boilers is lower than in the second fraction.

Figure 2:
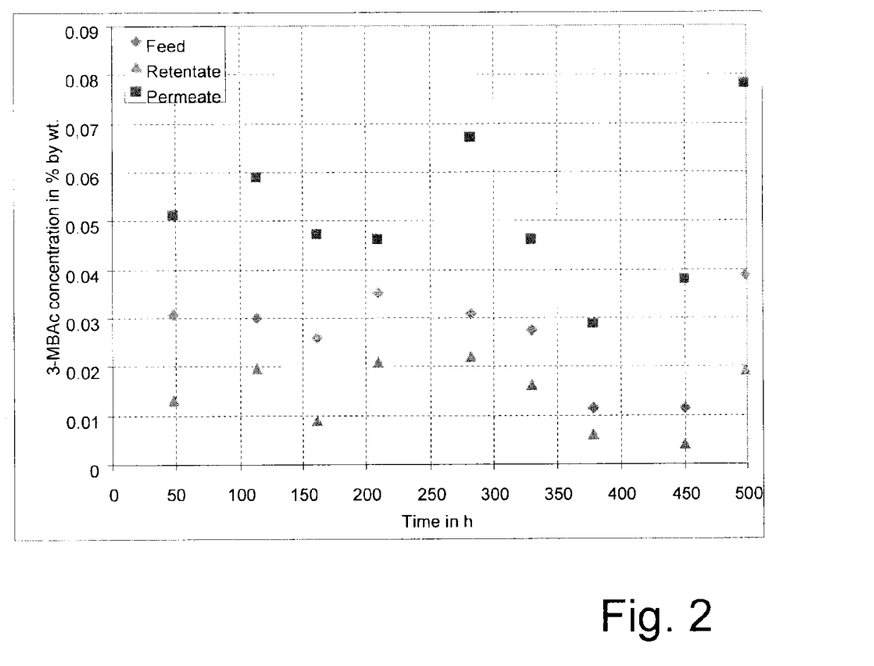
FIG. 2: graph of 3 MBAc concentrations in the feed, retentate and permeate of the nanofiltration.
Figure 3:
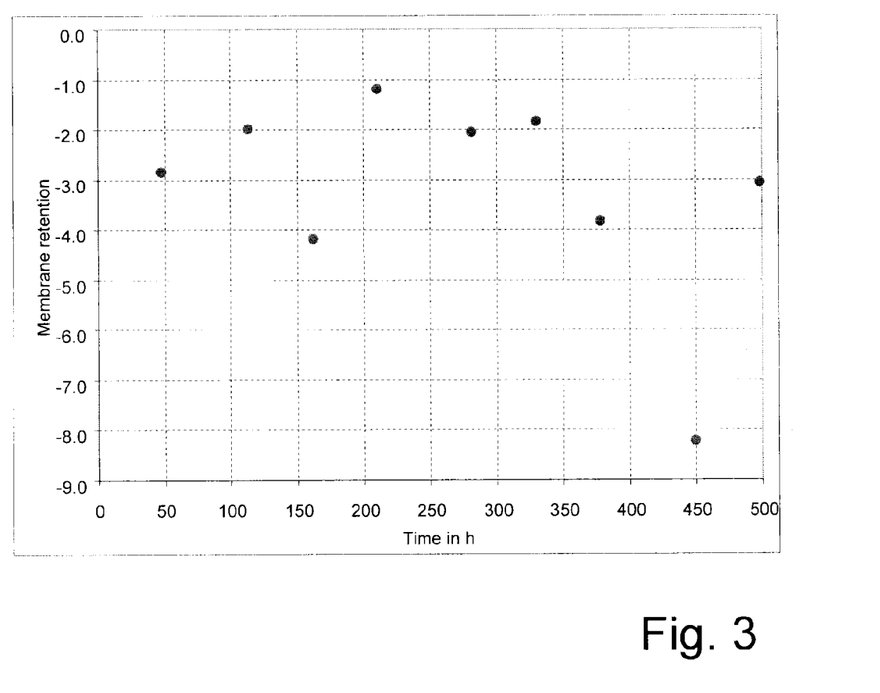
FIG. 3 graph of the 3 MBAc retention of the nanofiltration.

FIG. 2 shows the 3 MBAc concentration in the feed, retentate and permeate of the nanofiltration M over a period of 500 hours. FIG. 3 shows distinctly negative retentions of the Starmem 122 membrane used for the 3-MBAc in the nanofiltration step. The retention is defined as 1−(permeate concentration)/(retentate concentration).

LIST OF REFERENCE NUMERALS

1 Hydrocarbon stream
2 Product mixture
3 Resulting retentate
4 Resulting permeate
5 First fraction
6 Second fraction
D Thermal separation device
R Hydroformylation reactor
M Nanofiltration device
P Sampler

The invention claimed is:

1. A method for preparing a product mixture from an isobutene-containing hydrocarbon stream and for separating the resulting product mixture, said method comprising:
  a) hydroformylating an isobutene-containing hydrocarbon stream in a hydroformylation reactor in the presence of a transition metal complex catalyst, thereby obtaining a product mixture comprising 3-methylbutanal, conversion products in the form of high boilers, 3-methylbutanoic acid, the transition metal complex catalyst, and the free ligands thereof,
  b) separating the product mixture with a nanofiltration device comprising one or more membrane separation stages, such that the transition metal complex catalyst and the free ligands thereof are enriched in the resulting retentate of the nanofiltration device with respect to 3-methylbutanal and 3-methylbutanoic acid, and such that 3-methylbutanal and 3-methylbutanoic acid are each enriched in the resulting permeate of the nanofiltration device with respect to the transition metal complex catalyst, the concentration of the 3-methylbutanoic acid being lower in the resulting retentate than in the permeate,
  c) separating the resulting permeate of the nanofiltration device with a thermal separating device comprising one or more separation stages into at least one first fraction and a second fraction, wherein the first fraction has a higher concentration of 3-methylbutanal than the second fraction and a lower concentration of conversion products in the form of high boilers and 3-methylbutanoic acid than the second fraction, and
  d) recycling at least a substream of the resulting retentate of the nanofiltration device into the hydroformylation reactor, wherein:
  one or more nanofiltration membranes are used in the nanofiltration device; and
  the one or more membranes has a retention for 3-methylbutanoic acid of −1 or less.

2. The method according to claim 1, wherein:
  one or more process parameters in a) are set such that the total concentration of conversion products in the form of high boilers and 3-methylbutanoic acid, based on the weight of the overall product mixture, is 30% by weight or less; and
  the parameter(s) to be set are selected from the group consisting of pressure, temperature, mean residence time, composition of the synthesis gas, concentration of the transition metal and transition metal-ligand ratio of the transition metal complex catalyst.

3. The method according to claim 1, wherein a) is performed with at least one of
  a pressure in the range from 0.2 to 8 MPa,
  a temperature in the range from 70 to 130° C.,
  a mean residence time in the range from 1 to 4 h,
  a synthesis gas composition $CO:H_2$ of 1:3 to 3:1, and/or
  a transition metal concentration in the range from 10 to 100 ppm, and
  a transition metal/ligand ratio in the range from 1:4 to 1:50.

4. The method according to claim 1, wherein at least one of the following conditions is satisfied
  the transition metal of the transition metal complex catalyst is rhodium, and
  the ligand(s) of the transition metal complex catalyst is/are selected from the group
  consisting of organophosphorus ligands.

5. The method according to claim 1, wherein the transition metal of the transition metal complex catalyst is rhodium or cobalt.

6. The method according to claim 1, wherein the one or more membranes has a retention for 3-methylbutanoic acid of −5 or less.

7. The method according to claim 1, wherein:
  the one or more nanofiltration membranes comprise one or more polymers which comprise imide groups; and
  said polymers are selected such that the retention of the nanofiltration membrane for 3-methylbutanoic acid is −1 or less.

8. The method according to claim 1, wherein the one or more nanofiltration membranes have a separation limit of from 150 to 2000 g/mol.

9. The method according to claim 1, wherein:
  one or more nanofiltration membranes in the nanofiltration device comprise one or more polymers which comprise imide groups; and
  said polymers being selected such that the separation limit of the nanofiltration membrane is from 150 to 2000 g/mol.

10. The method according to claim 1, wherein b) is performed
  at a temperature in the range from 10 to 150° C.,
  and/or
  at a transmembrane pressure in the range from 0.5 to 6 MPa,
  and/or
  at a Reynolds number between 55 and 13 500,
  and/or
  in the presence of carbon monoxide and/or hydrogen in the feed, in the retentate and in the permeate of each membrane separation stage.

11. The method according to claim 1, wherein the thermal separation comprises a distillation in which the first fraction is obtained as the top product and the second fraction as the bottom product.

12. The method according to claim 1, comprising:
hydroformylating an isobutenic hydrocarbon stream in the presence of a rhodium complex catalyst having one or more organophosphorus ligands at a pressure in the range from 0.2 to 8 MPa and a temperature in the range from 70 to 130° C. with a mean residence time in the range from 1 to 4 h, a synthesis gas composition $CO:H_2$ of 1:3 to 3:1, a rhodium concentration in the reactor in the range from 10 to 100 ppm and a rhodium/ligand ratio in the range from 1:4 to 1:50,
separating the product mixture of the hydroformylation with a nanofiltration device at a temperature in the range from 10 to 150° C., a transmembrane pressure in the range from 0.5 to 6 MPa, at a Reynolds number between 170 and 900, and a partial carbon monoxide pressure of greater than 0.2 MPa into feed, retentate and permeate of each membrane separation stage,
thermally separating the resulting permeate of the nanofiltration device by distillation into a first fraction and a second fraction, wherein the first fraction comprises a higher concentration of 3-methylbutanal than the second fraction and a lower concentration of high boilers than the second fraction, and
recycling at least a substream of the resulting retentate of the nanofiltration device into the hydroformylation reactor.

13. The method according to claim 1, further comprising monitoring the concentration of 3-methylbutanoic acid in the resulting retentate of the nanofiltration device, and optionally in the product mixture and/or in the resulting permeate of the nanofiltration device.

14. The method according to claim 13, wherein, on exceedance of a fixed maximum concentration of the 3-methylbutanoic acid in the resulting retentate of the nanofiltration device, the recycling of the resulting retentate into the hydroformylation reactor is stopped.

15. The method according to claim 13, wherein, on exceedance of a fixed maximum concentration of 3-methylbutanoic acid in the feed of the nanofiltration device, one or more process parameters in a) are modified such that the concentration of 3-methylbutanoic acid in the feed of the nanofiltration device is lowered below the fixed maximum.

16. An apparatus for performance of the process according to claim 1, comprising
a hydroformylation reactor for hydroformylation of an isobutenic hydrocarbon stream in the presence of a transition metal complex catalyst,
a nanofiltration device comprising one or more membrane separation stages for separation of the product mixture formed in the hydroformylation reactor, such that the transition metal complex catalyst and the free ligands thereof are enriched in the resulting retentate of the nanofiltration device with respect to 3-methylbutanal and 3-methylbutanoic acid, and 3-methylbutanal and 3-methylbutanoic acid are enriched in the resulting permeate of the nanofiltration device with respect to the transition metal complex catalyst, such that the concentration of 3-methylbutanoic acid in the resulting retentate is lower than in the resulting permeate, the nanofiltration device comprising one or more nanofiltration membranes, and at least one of the nanofiltration membranes has a retention for 3-methylbutanoic acid of −1 or less,
at least one thermal separation device for thermal separation of the resulting permeate of the nanofiltration device into a first fraction and a second fraction, the first fraction having a higher concentration of 3-methylbutanal than the second fraction and a lower concentration of conversion products in the form of high boilers and 3-methylbutanoic acid than the second fraction, and
a way to recycle at least a substream of the resulting retentate of the nanofiltration device into the hydroformylation reactor.

17. The apparatus according to claim 16, further comprising
an apparatus to determine the concentration of 3-methylbutanoic acid in the retentate of the nanofiltration device, and optionally a device to determine the concentration of 3-methylbutanoic acid in the resulting product mixture of the hydroformylation and/or in the feed of the nanofiltration device and/or a device to determine the concentration of 3-methylbutanoic acid in the permeate of the nanofiltration device,
or
a device for taking samples from the retentate of the nanofiltration device, and optionally a device for taking samples from the resulting product mixture of the hydroformylation and/or from the feed of the nanofiltration device and/or a device for taking samples from the permeate of the nanofiltration device.

18. The apparatus according to claim 16, wherein the nanofiltration device comprises one or more nanofiltration membranes, and at least one of the nanofiltration membranes has a separation limit in the range from 150 to 2000 g/mol.

19. A method for preparation of a product mixture by industrial hydroformylation of an isobutene-containing hydrocarbon stream and for separation of the resulting product mixture, said method comprising the use of the apparatus of claim 16.

20. The method according to claim 10, wherein the partial pressure of carbon monoxide is at least 200 kPa in the feed, in the retentate and in the permeate of each membrane separation stage.

* * * * *